United States Patent
Agrawal et al.

(10) Patent No.: US 7,105,495 B2
(45) Date of Patent: Sep. 12, 2006

(54) MODULATION OF OLIGONUCLEOTIDE CPG-MEDIATED IMMUNE STIMULATION BY POSITIONAL MODIFICATION OF NUCLEOSIDES

(75) Inventors: Sudhir Agrawal, Shrewsbury, MA (US); Ekambar R. Kandimalla, Southboro, MA (US)

(73) Assignee: Idera Pharmaceuticals, Inc., Cambridge, MA (US)

( * ) Notice: Subject to any disclaimer, the term of this patent is extended or adjusted under 35 U.S.C. 154(b) by 76 days.

(21) Appl. No.: 10/406,015

(22) Filed: Apr. 3, 2003

(65) Prior Publication Data

US 2003/0236211 A1     Dec. 25, 2003

Related U.S. Application Data

(62) Division of application No. 09/845,623, filed on Apr. 30, 2001.

(51) Int. Cl.
*A01N 43/04* (2006.01)
*C12Q 1/68* (2006.01)
*C12N 15/63* (2006.01)

(52) U.S. Cl. ............................ 514/44; 514/42; 514/43; 514/45; 514/48; 514/49; 514/52; 514/885; 424/1.11; 424/1.73; 424/1.77; 424/9.81; 424/278.1; 424/280.1; 536/22.1; 536/23.1; 536/24.5; 536/25.6

(58) Field of Classification Search .............. 424/1.11, 424/1.73, 1.77, 278.1, 280.1; 514/42, 43, 514/44, 45, 48, 49, 52, 885
See application file for complete search history.

(56) References Cited

U.S. PATENT DOCUMENTS

| 5,149,798 A | | 9/1992 | Agrawal et al. |
| 5,663,153 A | * | 9/1997 | Hutcherson et al. ........... 514/44 |
| 5,719,271 A | * | 2/1998 | Cook et al. ................. 536/23.1 |
| 5,856,462 A | * | 1/1999 | Agrawal ..................... 536/24.5 |
| 5,968,909 A | * | 10/1999 | Agrawal et al. ............... 514/44 |

FOREIGN PATENT DOCUMENTS

| WO | WO 97/33992 | * | 9/1997 |
| WO | WO 98/49288 | | 11/1998 |
| WO | WO 01/12804 A2 | | 2/2001 |

OTHER PUBLICATIONS

Liang et al., J. Clin. Invest., vol. 98, pp. 1119-1129, 1996.*
Moldoveanu et al., Vaccine, vol. 16, pp. 1216-124, 1998.*
Yu et al., J. Med. Chem. vol. 45, pp. 4540-4548, 2002.*
Clivio et al., "Synthesis and Purification of Oligonucleotides Containing Sulfur Substituted Nucleobases: 4-Thiouracil, 4-Thiothymine, and 6-Mercaptopurine", Tetrahedron Letters, vol. 33, No. 1, pp. 65-68, 1992.*
Agrawal, Methods in Molecular Biology, Protocols for Oligonucleotides and Analogs, 20:165-189, (1993).
Agrawal et al., Curr. Op. in Biotech., 6:12 (1995).
Khorana et al., J. Molec. Biol. 72:209 (1972).

(Continued)

*Primary Examiner*—Shaojia Anna Jiang
*Assistant Examiner*—Traviss C. McIntosh
(74) *Attorney, Agent, or Firm*—Keown & Associates

(57) ABSTRACT

The invention provides methods for modulating the immune response caused by CpG dinucleotide-containing compounds. The methods according to the invention enables both decreasing the immunostimulatory effect for antisense applications, as well as increasing the immunostimulatory effect for immunotherapy applications.

3 Claims, 7 Drawing Sheets

Guanosine Modifications used in the study

OTHER PUBLICATIONS

Reese, Tetrahedron Lett. 34:3143-3179 (1978).
Beaucage et al., Tetrahedron Lett. 22:1859-1862 (1981).
Agrawal et al., Tetrahedron Lett. 28:3539-3542 (1987).
Connolly et al., Biochemistry 23:3443 (1984).
Jager et al., Biochemistry 27:7237 (1988).
Agrawal et al., Proc. Natl. Acad. Sci. USA 85:7079-7083 (1988).
McIntyre et al., Antisense Res. Dev. 3:309-322 (1993).
Kuramoto et al., Jpn. J. Cancer Res. 83:1128-1131 (1992).
Krieg et al., Nature 371:546-549 (1995).
Liang et al., J. Clin. Invest. 98:1119-1129 (1996).
Moldoveanu et al., Vaccine 16:1216-124.
McCluskie et al., The Journal of Immunology 161:4463-4466 (1998).
Zhao, Q. et al., Bioorganic & Medicinal Chemistry, "Site of Chemical Modifications in CpG Containing Phosphorothioate Oligonucleotide Modulates Its Immunostimulatory Activity", pp. 3453-3459 (1999).
Krieg, Arthur M., Applied Antisense Oligonucleotide Technology, "Leukocyte Stimulation by Oligodeoxynucleotides", pp. 431-448 (1998).
Kandimalla, E.R. et al., Bioorganic & Medicinal Chemistry, "Effect of chemical Modifications of Cytosine and Guanine in a CpG-Motif of Oligonucleotides: Structure-Immunostimulatory Activity Relationships", pp. 807-813 (2001).
Ekambar, D.Y. et al., Bioorganic & Medicinal Chemistry, "Modulation of Immunostimulatory Activity of CpG Oligonucleotides by Site-Specific Deletion of Nucleobases", pp. 2263-2267 (2001).
Khorana et al. "Studies on Polynucleotides", J. Molec. Biol. 72:209 (1972).
Agrawal et al., "Oligodeoxynucleotides Methylphosphonates: Synthesis and Enzymic Degradation", Tetrahedron Lett. 28(31):3539-4542 (1987).
Zon et al., "Phosphorothioate Oligonucleotides" Oligonucleotides and Analogues: A Practical Approach, pp. 87-108 (1991).
Agrawal, "Antisense Oligonucleotides and Antiviral Agents", Trends in Biotechnology, 10:152-158 (1992).
Zon, "Protocols for Oligonucleotides and Analogs," Methods in Molecular Biology, 20:165-189 (1993).
Agrawal et al., "Antisense Therapeutics: Is It as Simple as Complementary Base Recognition?" Mol. Med. Today 6:72-81 (2000).

* cited by examiner

Guanosine Modifications used in the study

Inosine

2-NH$_2$-Purine

Nebularine

G$^{7\text{-deaza}}$

G$^{iso}$

5'-NNNNNX1X2CGX3X4NNNNN-3'.

Abasic (1', 2'-deoxyribose)

Oligo 91-3: $X_1$ = R, $X_2$ = A, $X_3$ = T, $X_4$ = T

Oligo 91-4: $X_2$ = R, $X_1$ = G, $X_3$ = T, $X_4$ = T

1',2'-Dideoxyribose Substitution

| HYB No. | Sequences and Modification (5'-3') | Batch No. |
|---|---|---|
| HYB1158 | CTATCTGA<u>CG</u>TTCTCTGT | D7-131-1 |
| HYB1160 | CTAXXTGACGTTCTCTGT | D7-131-12 |
| HYB1161 | CTATCTGAXGTTCTCTGT | D7-131-13 |

X =

1',2'-Dideoxyribose Substitution

| HYB No. | Sequences and Modification (5'-3') | Batch No. |
|---|---|---|
| HYB1159 | CCTACTAG<u>CG</u>TTCTCATC | D7-133-1 |
| HYB1162 | CCTXXTAGCGTTCTCATC | D7-133-12 |
| HYB1163 | CCTACTAGXGTTCTCATC | D7-133-13 |

SEQUENCE LISTING

```
<160> NUMBER OF SEQ ID NOS: 6

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ctatctgacg ttctctgt                                                      18

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: a, t, c, g, other or unknown

<400> SEQUENCE: 2
ctanntgacg ttctctgt                                                      18

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)
<223> OTHER INFORMATION: a, t, c, g, other or unknown

<400> SEQUENCE: 3
ctatctgang ttctctgt                                                      18

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
cctactagcg ttctcatc                                                      18

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

-continued

```
<221> NAME/KEY: modified_base
<222> LOCATION: (4)..(5)
<223> OTHER INFORMATION: a, t, c, g, other or unknown

<400> SEQUENCE: 5
cctnntagcg ttctcatc                                                18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)
<223> OTHER INFORMATION: a, t, c, g, other or unknown

<400> SEQUENCE: 6
cctactagng ttctcatc                                                18
```

MODULATION OF OLIGONUCLEOTIDE CPG-MEDIATED IMMUNE STIMULATION BY POSITIONAL MODIFICATION OF NUCLEOSIDES

BACKGROUND OF THE INVENTION

1. Field of the Invention

The invention relates to the therapeutic use of oligonucleotides, both in the antisense approach, and as immunostimulatory agents.

2. Summary of the Related Art

Oligonucleotides have become indispensible tools in modern molecular biology, being used in a wide variety of techniques, ranging from diagnostic probing methods to PCR to antisense inhibition of gene expression. This widespread use of oligonucleotides has led to an increasing demand for rapid, inexpensive and efficient methods for synthesizing oligonucleotides.

The synthesis of oligonucleotides for antisense and diagnostic applications can now be routinely accomplished. See e.g., *Methods in Molecular Biology*, Vol 20: *Protocols for Oligonucleotides and Analogs* pp. 165–189 (S. Agrawal, Ed., Humana Press, 1993); *Oligonucleotides and Analogues: A Practical Approach*, pp. 87–108 (F. Eckstein, Ed., 1991); and Uhlmann and Peyman, supra. Agrawal and Iyer, *Curr. Op. in Biotech.* 6: 12 (1995); and *Antisense Research and Applications* (Crooke and Lebleu, Eds., CRC Press, Boca Raton, 1993). Early synthetic approaches included phosphodiester and phosphotriester chemistries. Khorana et al., *J. Molec. Biol.* 72: 209 (1972) discloses phosphodiester chemistry for oligonucleotide synthesis. Reese, *Tetrahedron Lett.* 34: 3143–3179 (1978), discloses phosphotriester chemistry for synthesis of oligonucleotides and polynucleotides. These early approaches have largely given way to the more efficient phosphoramidite and H-phosphonate approaches to synthesis. Beaucage and Caruthers, *Tetrahedron Lett.* 22: 1859–1862 (1981), discloses the use of deoxynucleoside phosphoramidites in polynucleotide synthesis. Agrawal and Zamecnik, U.S. Pat. No. 5,149,798 (1992), discloses optimized synthesis of oligonucleotides by the H-phosphonate approach.

Both of these modern approaches have been used to synthesize oligonucleotides having a variety of modified internucleotide linkages. Agrawal and Goodchild, *Tetrahedron Lett.* 28: 3539–3542 (1987), teaches synthesis of oligonucleotide methylphosphonates using phosphoramidite chemistry. Connolly et al., *Biochemistry* 23: 3443 (1984), discloses synthesis of oligonucleotide phosphorothioates using phosphoramidite chemistry. Jager et al., *Biochemistry* 27: 7237 (1988), discloses synthesis of oligonucleotide phosphoramidates using phosphoramidite chemistry. Agrawal et al., *Proc. Antl. Acad. Sci. USA* 85: 7079–7083 (1988), discloses synthesis of oligonucleotide phosphoramidates and phosphorothioates using H-phosphonate chemistry.

More recently, several researchers have demonstrated the validity of the antisense approach to therapeutic treatment of disease. Crooke, Antisense Nucleic Acid Drug Dev. 8: vii–viii, discloses the successful marketing approval of a phosphorothioate oligonucleotide for the treatment of human cytomegalovirus-induced retinitis. Unfortunately, the use of phosphorothioate oligonucleotides has become more complex than originally expected. Certain effects caused by phosphorothioate oligonucleotides could not be explained by the expected antisense mechanism. For example, McIntyre et al., Antisense Res. Dev. 3: 309–322 (1993) teaches that a "sense" phosphorothioate oligonucleotide causes specific immune stimulation. This and other side effects have complicated the picture for phosphorothioate oligonucleotides.

On the other hand, the observation that phosphodiester and phosphorothioate oligonucleotides can induce immune stimulation has created interest in developing this side effect as a therapeutic tool. These efforts have focussed on phosphorothioate oligonucleotides containing the dinucleotide CpG. Kuramoto et al., Jpn. J. Cancer Res. 83: 1128–1131 (1992) teaches that phosphodiester oligonucleotides containing a palindrome that includes a CpG dinucleotide can induce interferon-alpha and gamma synthesis and enhance natural killer activity. Krieg et al., Nature 371: 546–549 (1995) discloses that phosphorothioate CpG-containing oligonucleotides are immunostimulatory. Liang et al., J. Clin. Invest. 98: 1119–1129 (1996) discloses that such oligonucleotides activate human B cells. Moldoveanu et al., Vaccine 16: 1216–124 (1998) teaches that CpG-containing phosphorothioate oligonucleotides enhance immune response against influenza virus. McCluskie and Davis, The Journal of Immunology 161: 4463–4466 (1998) teaches that CpG-containing oligonucleotides act as potent adjuvants, enhancing immune response against hepatitis B surface antigen.

These reports make clear that there is a need to be able to modulate the immune response caused by CpG-containing oligonucleotides. Ideally, such modulation should include decreasing the immunostimulatory effect for antisense applications, as well as increasing the immunostimulatory effect for immunotherapy applications.

BRIEF SUMMARY OF THE INVENTION

The invention provides methods for modulating the immune response caused by CpG dinucleotide-containing compounds. The methods according to the invention enable both decreasing the immunostimulatory effect for antisense applications, as well as increasing the immunostimulatory effect for immunotherapy applications. Thus, the invention further provides compounds having optimal levels of immunostimulatory effect for either application and methods for making and using such oligonucleotides.

The present inventor has surprisingly discovered that positional modification of CpG-containing oligonucleotides dramatically affects their immunostimulatory capabilities. In particular, 2' or 3' sugar or base modifications of oligonucleotides, or introduction of a modified internucleoside linkage, at particular positions 5' or 3', including 5' or 3' end modifications, to the CpG dinucleotide either enhances or reduces their immunostimulatory effect in a reproducible and predictable manner.

In a first aspect, the invention provides a method for modulating the immunostimulatory effect of a CpG dinucleotide containing compound by introducing an immunomodulatory moiety at a position either 5' to or 3' to the CpG dinucleotide.

In a second aspect, the invention provides compounds having increased or reduced immunostimulatory effect, the compounds comprising a CpG dinucleotide and an immunomodulatory moiety, wherein the increased or reduced immunomodulatory effect is relative to a similar compound lacking the immunomodulatory moiety.

In a third aspect, the invention provides a method for obtaining an antisense-specific reduction in the expression of a gene in a mammal, including a human, the method comprising administering to the mammal an oligonucleotide that is complementary to the gene and which comprises a CpG dinucleotide and an immunomodulatory moiety, wherein the oligonucleotide has less immunostimulatory effect than a similar oligonucleotide lacking the immunomodulatory moiety.

In a fourth aspect, the invention provides a method for inducing an immune response in a mammal, including a human, the method comprising administering to the mammal a compound comprising a CpG dinucleotide and and an immunomodulatory moiety, wherein the compound has greater immunostimulatory effect than a similar compound lacking the immunomodulatory moiety.

Figure 1A:
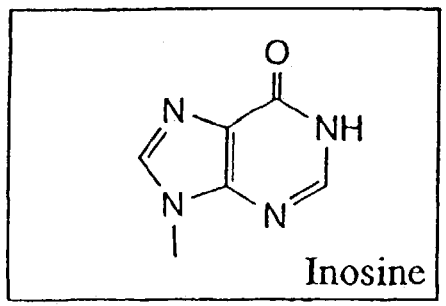
FIG. 1 shows preferred embodiments of immunomodulatory moieties according to the invention. Note that the Figures use X3X4 for the 3' side and X1X2 for the 5' side. This use is illustrative for this figure only and should not be used to interpret the claims, which use the Y and X designations taught in this specification.
Figure 1A:
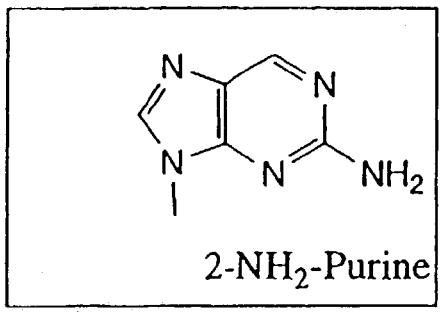
Figure 1A:
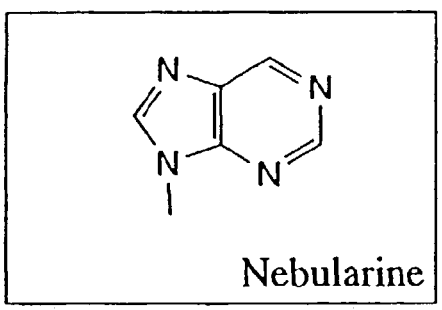
Figure 1A:
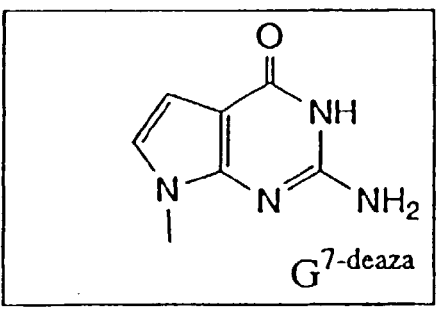
Figure 1A:
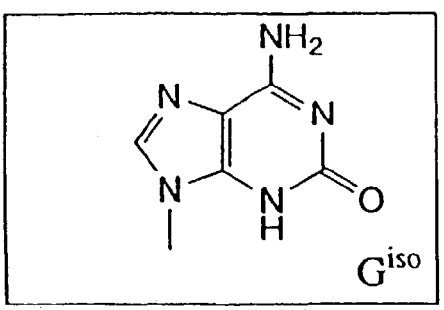

DETAILED DESCRIPTION OF THE
PREFERRED EMBODIMENTS

The invention relates to the therapeutic use of oligonucleotides, both in the antisense approach, and as immunostimulatory agents. The patents and publications cited herein reflect the level of knowledge in the field and are hereby incorporated by reference in their entirety. In the event of conflict between any teaching of any reference cited herein and the present specification, the latter shall prevail, for purposes of the invention.

The invention provides methods for modulating the immune response caused by CpG dinucleotide-containing compoundss. The methods according to the invention enable both decreasing the immunostimulatory effect for antisense applications, as well as increasing the immunostimulatory effect for immunotherapy applications. Thus, the invention further provides oligonucleotides having optimal levels of immunostimulatory effect for either application and methods for making and using such oligonucleotides.

The present inventor has surprisingly discovered that positional modification of CpG-containing oligonucleotides dramatically affects their immunostimulatory capabilities. In particular, 2' or 3' sugar or base modifications of oligonucleotides, or introduction of a modified internucleoside linkage, at particular positions 5' or 3' to the CpG dinucleotide, including 5' or 3' end modifications, or combinations thereof, either enhances or reduces their immunostimulatory effect in a reproducible and predictable manner.

In a first aspect, the invention provides a method for modulating the immunostimulatory effect of a CpG dinucleotide containing compound by introducing an immunomodulatory moiety at a position either 5' to or 3' to the CpG dinucleotide. Preferred compounds according to this aspect of the invention generally include additional oligonucleotide sequences.

In certain preferred embodiments the method is used to make an oligonucleotide that is complementary to a gene or gene transcript. In certain preferred embodiments, the oligonucleotide has antisense activity. In some preferred embodiments, only one immunomodulatory moiety is introduced into the oligonucleotide for each CpG dinucleotide present in the oligonucleotide. In some preferred embodiments, only one immunomodulatory moiety is introduced into the oligonucleotide.

In certain preferred embodiments, the oligonucleotide made according to this aspect of the invention does not have antisense activity and/or is not complementary to a gene.

As herein, the term "complementary" means having the ability to hybridize to a genomic region, a gene, or an RNA transcript thereof under physiological conditions. Such hybridization is ordinarily the result of base-specific hydrogen bonding between complementary strands, preferably to form Watson-Crick or Hoogsteen base pairs, although other modes of hydrogen bonding, as well as base stacking can also lead to hybridization. As a practical matter, such hybridization can be inferred from the observation of specific gene expression inhibition.

As used herein, "antisense activity" means that the oligonucleotide, when introduced into a cell or an animal, causes a reduction in the expression of the gene to which it is complementary.

The method according to this aspect of the invention can be conveniently carried out using any of the well-known synthesis techniques by simply using an appropriate immunomodulatory moiety monomer synthon in the synthesis process in a cycle following, immediately or otherwise the incorporation of the CpG dinucleotide. Preferred monomers include phosphoramidites, phosphotriesters and H-phosphonates.

For purposes of the invention, "introducing an immunomodulatory moiety into position Y2" simply means synthesizing an oligonucleotide that has an immunomodulatory moiety at such a position, with reference to the following structure:

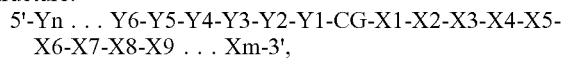

wherein C is cytosine, G is guanosine, a substituted guanosine, including inosine and 7-deazaguanosine, and each X and Y is independently a nucleoside or an immunomodulatory moiety, and n is a number from –9 to +20, and m is a number from –6 to +20.

Procedures for synthesis of oligonucleotides are well known in the art.

In a second aspect, the invention provides compounds having increased or reduced immunostimulatory effect, the compounds comprising a CpG dinucleotide and an immunomodulatory moiety, wherein the increased or reduced immunostimulatory effect is relative to a similar compound lacking the immunomodulatory moiety. Preferred compounds according to this aspect of the invention generally include additional oligonucleotide sequences. Preferably, such oligonucleotide sequences will have from about 6 to about 50 nucleotides, most preferably from about 12 to about 35 nucleotides.

Certain preferred compounds according to the invention have the structure:

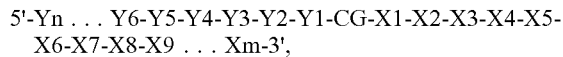

wherein C is cytosine, G is guanosine, a substituted guanosine, including inosine and 7-deazaguanosine, and each X and Y is independently a nucleoside or an immunomodulatory moiety, and n is a number from –9 to +20, and m is a number from –6 to +20.

In particularly preferred embodiments, the base sequence that is modified to provide the compound is

5'-CTATCTGACGTTCTCTGT-3' (SEQ ID NO: 1)

or

5'-CCTACTAGCGTTCTCATC-3' (SEQ ID NO: 4)

Preferred immunomodulatory moieties include one or more abasic nucleoside, 1,3-propanediol linker (substituted or unsubstituted), and/or modified base-containing nucleosides, including Hexa (ethylene glycol), nitropyrrole, nitroindole, deoxyuridine, inosine, isoguanosine, 2-aminopurine, nebularine, 7-deazaguanosine, 4-thiodeoxyuridine, 4-thiothymidine, d-isoguanosine, d-iso-5-methylcytosine, P-base, and 3'—3' linkage. As a general rule, introduction of an immunomodulatory moiety at position Y6, Y5, Y4, or Y3, or a combination thereof, increases the immunostimulatory effect of the oligonucleotide. Generally, introduction of an immunomodulatory moiety at position Y2 maintains immunostimulatory effect. Generally, introduction of an immunomodulatory moiety at position Y1 maintains or reduces immunostimulatory effect. Generally, introduction of an immunomodulatory moiety at position C abolishes immunostimulatory effect. Generally, introduction of an immunomodulatory moiety at position G abolishes immunostimulatory effect, except for 7-deazaguanosine, which maintains immunostimulatory effect. Generally, introduction of an immunomodulatory moiety at position X1 maintains or reduces immunostimulatory effect. Generally, introduction of an immunomodulatory moiety at position X2 has little impact on immunostimulatory effect. Generally, introduction of an immunomodulatory moiety at position X3 maintains or increases immunostimulatory effect. Generally, introduction of an immunomodulatory moiety at position X4, X5, X6, X7-Xm, or any combination thereof, increases immunostimulatory effect.

Certain preferred oligonucleotides according to this aspect of the invention are complementary to a gene or gene transcript. More preferably, such oligonucleotides have antisense activity. In some preferred embodiments, the oligonucleotide has only one immunomodulatory moiety for each CpG dinucleotide present in the oligonucleotide. In some preferred embodiments, the oligonucleotide has only one immunomodulatory moiety. In other preferred embodiments, the compounds according to this aspect of the invention do not have antisense activity and/or are not complementary to a gene.

In a third aspect, the invention provides a method for obtaining an antisense-specific reduction in the expression of a gene in a mammal, including a human, the method comprising administering to the mammal an oligonucleotide that is complementary to the gene and which comprises a CpG dinucleotide and an immunomodulatory moiety, wherein the oligonucleotide has less immunostimulatory effect than a similar oligonucleotide lacking the immunomodulatory moiety.

In some preferred embodiments, the oligonucleotide has only one immunomodulatory moiety for each CpG dinucleotide present in the oligonucleotide. In some preferred embodiments, the oligonucleotide has only one immunomodulatory moiety.

In the methods according to this aspect of the invention, preferably, administration of antisense oligonucleotides should be parenteral, oral, sublingual, transdermal, topical, intranasal, intrtracheal, or intrarectal. Administration of the therapeutic compositions can be carried out using known procedures at dosages and for periods of time effective to reduce symptoms or surrogate markers of the disease. When administered systemically, the therapeutic composition is preferably administered at a sufficient dosage to attain a blood level of oligonucleotide from about 0.001 micromolar to about 10 micromolar. For localized administration, much lower concentrations than this may be effective, and much higher concentrations may be tolerated. Preferably, a total dosage of oligonucleotide will range from about 0.1 mg oligonucleotide per patient per day to about 200 mg oligonucleotide per kg body weight per day. It may be desirable to administer simultaneously, or sequentially a therapeutically effective amount of one or more of the therapeutic compositions of the invention to an individual as a single treatment episode. In a preferred embodiment, after the composition of matter is administered, one or more measurement is taken of biological effects selected from the group consisting of complement activation, mitogenesis and inhibition of thrombin clot formation.

The method according to this aspect of the invention is useful in animal models of disease or gene expression, and is further useful for the therapeutic treatment of human or animal disease.

In a fourth aspect, the invention provides a method for inducing an immune response in a mammal, including a human, the method comprising administering to the mammal a compound comprising a CpG dinucleotide and and an immunomodulatory moiety, wherein the compound has greater immunostimulatory effect than a similar compound lacking the immunomodulatory moiety.

In the methods according to this aspect of the invention, preferably, administration of compounds should be parenteral, oral, sublingual, transdermal, topical, intranasal, intratracheal, or intrarectal. Administration of the therapeutic compositions can be carried out using known procedures at dosages and for periods of time effective to reduce symptoms or surrogate markers of the disease. When administered systemically, the therapeutic composition is preferably administered at a sufficient dosage to attain a blood level of oligonucleotide from about 0.001 micromolar to about 10 micromolar. For localized administration, much lower concentrations than this may be effective, and much higher concentrations may be tolerated. Preferably, a total dosage of oligonucleotide will range from about 0.1 mg oligonucleotide per patient per day to about 200 mg oligonucleotide per kg body weight per day. It may be desirable to administer simultaneously, or sequentially a therapeutically effective amount of one or more of the therapeutic compositions of the invention to an individual as a single treatment episode. In a preferred embodiment, after the composition of matter is administered, one or more measurement is taken of biological effects selected from the group consisting of complement activation, mitogenesis and inhibition of thrombin clot formation.

In certain preferred embodiments, compounds according to the invention are administered in combination with vaccines, antibodies, cytotoxics, antisense oligonucleotides, gene therapy vectors, DNA vaccines and/or adjuvants to enhance the specificity or magnitude of the immune response. Either the compound or the vaccine, or both may optionally be linked to an immunogenic protein, such as keyhole limpet hemocyanin, cholera toxin B subunit, or any other immunogenic carrier protein. Any of the plethora of adjuvants may be used, including, without limitation, Freund's complete adjuvant. For purposes of this aspect "in combination with" means in the course of treating the same disease in the same patient, and includes administering the oligonucleotide and/or the vaccine and/or the adjuvant in any order, including simultaneous administration, as well as temporally spaced order of up to several days apart. Such combination treatment may also include more than a single administration of the oligonucleotide, and/or independently the vaccine, and/or independently the adjuvant. The administration of the oligonucleotide and/or vaccine and/or adjuvant may be by the same or different routes.

The method according to this aspect of the invention is useful for model studies of the immune system, and is further useful for the therapeutic treatment of human or animal disease.

For purposes of all aspects of the invention, the term "oligonucleotide" includes polymers of two or more deoxyribonucleotides, or any modified nucleoside, including 2'-halo-nucleosides, 2' or 3' substituted, 2' or 3'-O-substituted ribonucleosides, deazanucleosides or any combination thereof. Such monomers may be coupled to each other by any of the numerous known internucleoside linkages. In certain preferred embodiments, these internucleoside linkages may be phosphodiester, phosphotriester, phosphorothioate, or phosphoramidate linkages, 2'–5' linkages of any of the forgoing, or combinations thereof. The term oligonucleotide also encompasses such polymers having chemically modified bases or sugars and/or having additional substituents, including without limitation lipophilic groups, intercalating agents, diamines and adamantane. The term oligonucleotide also encompasses PNA, LNA and oligonucleotides comprising non-pentose sugar (e.g. hexose) backbones or backbone sections. For purposes of the invention the terms "2'-O-substituted" and "3'-O-substituted" mean (respectively) substitution of the 2' (or 3') position of the pentose moiety with a halogen (preferably Cl, Br, or F), or an -O-lower alkyl group containing 1–6 saturated or unsaturated carbon atoms, or with an -O-aryl or allyl group having 2–6 carbon atoms, wherein such alkyl, aryl or allyl group may be unsubstituted or may be substituted, e.g., with halo, hydroxy, trifluoromethyl, cyano, nitro, acyl, acyloxy, alkoxy, carboxyl, carbalkoxyl, or amino groups; or such 2' substitution may be with a hydroxy group (to produce a ribonucleoside), an amino or a halo group, but not with a 2' (or 3') H group. For purposes of all aspects of the invention, the terms "CpG" or "CpG dinucleotide" means the dinucleotide 5'-deoxycytidine-deoxyguanidine or deoxyguanidine analog-3', wherein p is an internucleotide linkage, and wherein the sugar backbone of the dinucleotide may be ribose, deoxyribose, or 2' substituted ribose, or combinations thereof. In preferred embodiments of the first three aspects of the invention, p is selected from phosphodiester, phosphorothioate, alkylphosphonate, phosphotriester, stereospecific (Rp or Sp) phosphorothioate or alkylphosphonate, and 2'–5' covalent linkages of any of the above. The non-phosphodiester, non-phosphorothioate embodiments will further reduce immunostimulatory effects. In preferred embodiments of the last three aspects of the invention, p is selected from phosphodiester, phosphorothioate and phosphordithioate.

The following examples are intended to further illustrate certain preferred embodiments of the invention, and are not intended to limit the scope of the invention.

Example 1

Modulation of Immulostimulatory Effect in Vitro

To study the impact of site of chemical modification of PS-oligos containing CpG motif, we chose two oligonucleotides. Oligo 1 and Oligo 2, each of which contains one CpG motif. To evaluate the immunostimulatory activity of oligonucleotides in the present study, we will use a mouse spleen cell proliferation assay.

Figures 1, 1B:
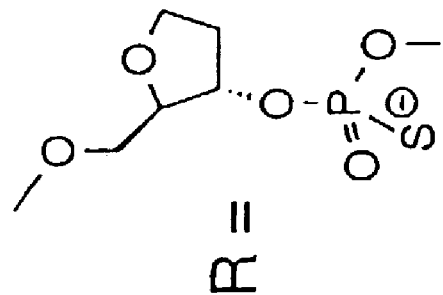

Mouse spleen lymphocytes are cultured with oligonucleotides at concentration of 0.1, 1, and 10 µg/mL. Oligo 1 and Oligo 2 will induce a dose dependent effect on cell proliferation. At 0.1 µg/mL, the proliferation index will increase. Substitution of 5'-flanking deoxynucleoside (Y1) of CpG motif of Oligo 1 or Oligo 2 with an immunomodulatory moiety according to the invention will result in complete suppression of cell proliferation at all concentrations used (FIG. 1). At 0.1 µg/mL, cell proliferation index will be similar to medium alone. Substitution of the 3'-flanking deoxynucleoside (X1) of CpG motif of Oligo 1 or Oligo 2 with 2'-OMe will not have such an impact on cell proliferation, but may reduce it slightly. Similar substitutions are made in Oligo 1 or Oligo 2 in the 3'-flanking region to CpG motif. Oligos are synthesized in which a deoxynucleoside is substituted with an immunomodulatory moiety according to the invention at position X3, X4, X5 or X6. The proliferation index of these oligos will increase.

Example 2

Effect of Immunomodulatory Moities on Spleen Weight

Figures 1, 1B, 2:
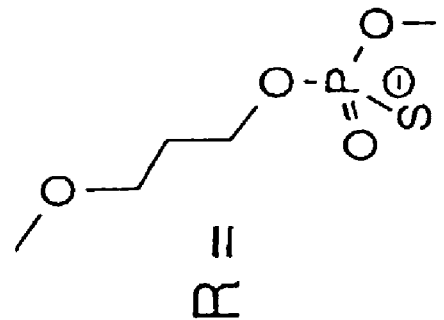
FIG. 2 (SEQ ID NOS 1–3, respectively, in order of appearance) shows a modified compound according to the invention and results of spleen assays using this compound.
Figures 1, 1B, 2, 3:
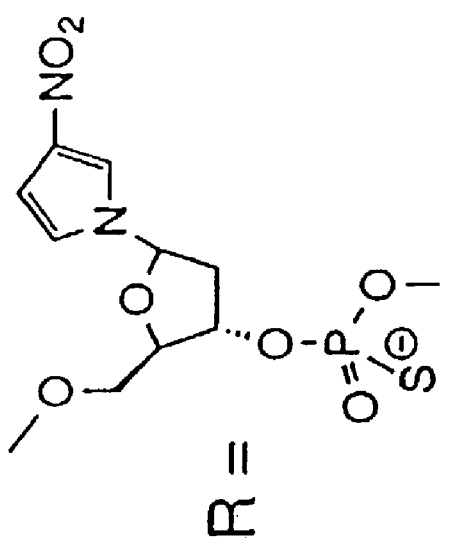
FIG. 3 (SEQ ID NOS 4–6, respectively, in order of appearance) shows another modified compound according to the invention and results of spleen assays using this compound.
Figures 1, 1B, 2, 3, 4:
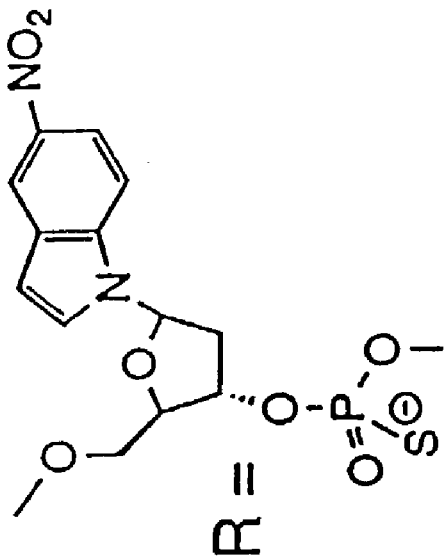
Figure 2A:
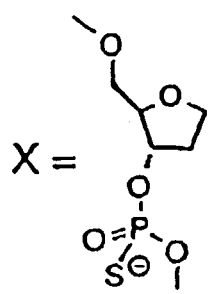
Figure 2B:
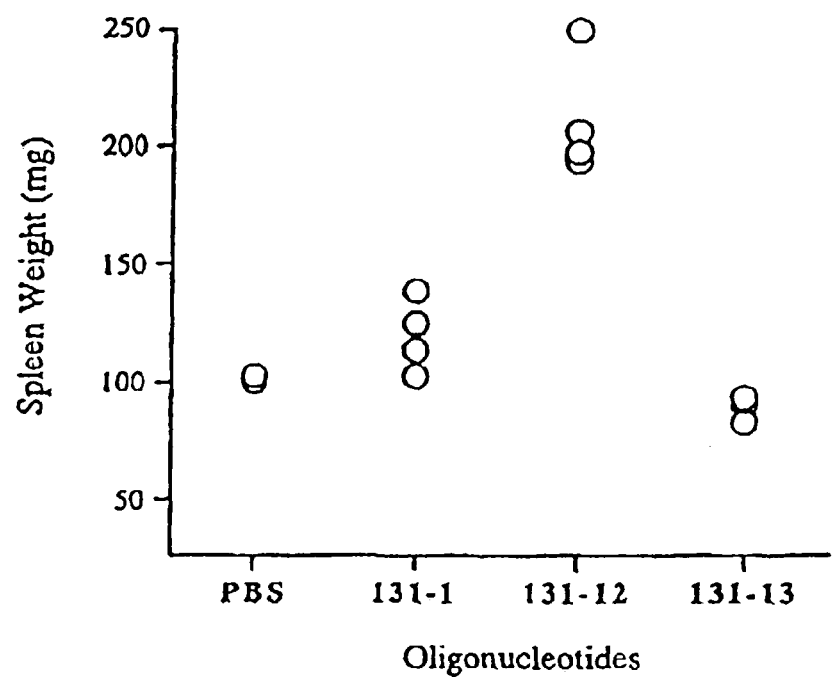
Figure 3A:
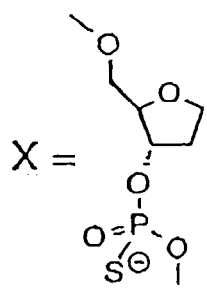
Figure 3B:
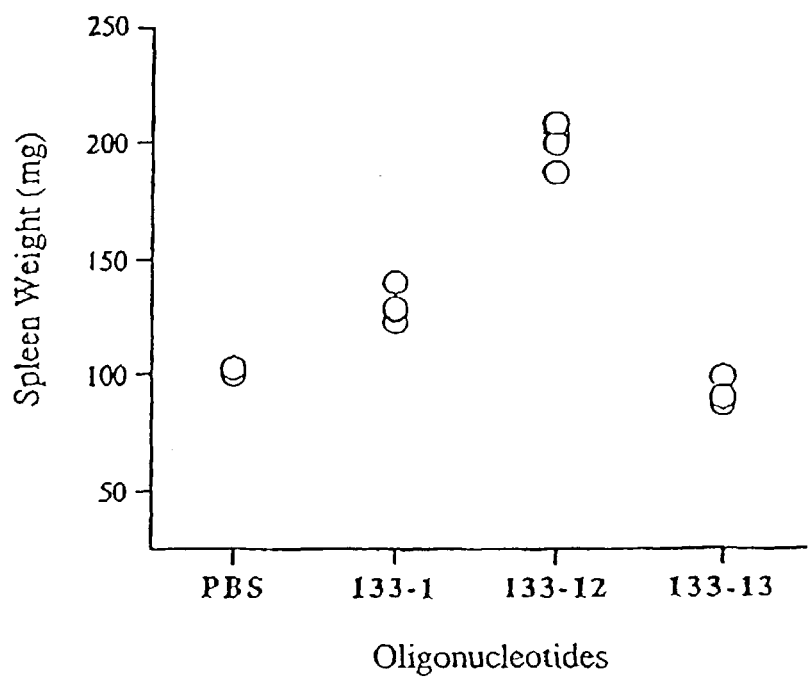

After observing that above substitutions in modulates its immunostimulatory activity based on cell culture assay, we administer oligonucleotides listed in Table 1 intraperitonealy to mice and measure the spleen weights to confirm that the substitutions have similar effects in vivo. Administration of Oligo 1 or Oligo 2 will cause substantial increase in spleen weight. Substitution of a deoxynucleotide away from CpG motif towards 5'-end, positions Y6, Y5, Y4 or Y3 will cause progressive increase in spleen weights confirming an increase in their immunostimulatory activity. Substitutions of a deoxynucleoside toward the 3'-end of the CpG motif, in general, will cause less significant increase in spleen weight. Data are shown in FIGS. 2 and 3.

Example 3

Synthesis of Oligonucleotides Containing Immunomodulatory Moieties

Oligonucleotides are synthesized on 1 micromolar scale using an automated DNA synthesizer (Expedite 8909, PerSeptive Biosystems, Foster City, Calif.). Standard deoxynucleoside phosphoramidites are obtained from PerSeptive Biosystems. 1',2'-dideoxyribose phosphoramidite, propyl-1-phosphoramidite, 2'-deoxy-5-nitroindole-ribofuranosyl phosphoramidite, deoxyuridine phosphoramidite, dP phosphoramidite, d-2-aminopurine phosphoramidite, d-nebularine phosphoramidite and d-7-deazaguanine phosphoramidite are obtained from Glen Research (Sterling, Va.). Deoxyinosine phosphoramidite is obtained from Chem-Genes (Ashland, Mass.). Normal coupling cyles are used for all phosphoramidites. Beaucage reagent is used as an oxidant to obtain phosphorothioate modification. After synthesis, oligonucleotides are deprotected by incubating CPG-bound oligonucleotide with concentrated ammonium hydroxide solution for 1.5–2 hours at room temperature and then incubating the ammonium hydroxide supernatant for 12 hours at 55 degrees C. The ammonium hydroxide solution is evaporated to dryness in a speed-vac and 5'-DMTr-oligonucleotides are purified by HPLC on a C18 reverse-phase matrix using a solvent system of 0.1 M ammonium acetate and 1:5 ratio 0.1 M ammonium acetate in acetonitrile. Then the oligonucleotides are treated with 80% acetic acid to remove the DMTr group, converted to sodium form and desalted by dialysis against distilled water. Oligonucleotides are lyophilized and redissolved in water. Characterization is achieved by denaturing PAGE and MALDI-TOF mass spectrometry.

---

What is claimed is:

1. A method for modulating the immunostimulatroy effect of a 5'-CpG-3' dinucleotide containing compound, wherein C is cytosine and G is guanosine or a substituted guanosine, by introducing an immunomodulatory moiety at a position either 5' or 3' to the CpG dinucleotide, wherein the immunomodulatory moiety is selected from the group consisting of abasic nucleoside, 1,3-propanediol linker, nitropyrrole, nitroindole, deoxyuridine, inosine, isoguanosine, 2-aminopurine, nebularine, 7-deazaguanosine. 4-thiodeoxyuridine, 4-thiothymidine, d-isoguanosine, d-iso-5-methylcytosine, P-base, and 3'—3' linkage, and wherein the compound is 12 to 35 nucleotides in length and wherein the compound does not have antisense activity.

2. The method according to claim 1, wherein the compound has the structure 5'-Yn . . . Y6-Y5-Y4-Y3-Y2-Y1-CG-X1-X2-X3-X4-X5-X6-X7-X8-X9 . . . Xm-3', wherein C is cytosine, G is guanosine, or a substituted guanosine, and each X and Y is independently a nucleoside or an immunomodulatory moiety, and n is a number from −6 to +20, and m is a number from −9 to +20.

3. The method according to claim 2, wherein G is inosine or 7-deazaguanosine.

* * * * *